United States Patent [19]

Dross et al.

[11] Patent Number: 5,728,118
[45] Date of Patent: Mar. 17, 1998

[54] APPARATUS AND METHOD FOR HARVESTING A BONE-TENDON-BONE LIGAMENT GRAFT

[75] Inventors: Brian David Dross, Huger, S.C.; William Palleva, Cerritos; Terry Van Blaricom, Sherman Oaks, both of Calif.

[73] Assignee: Linvatec Corporation, Largo, Fla.

[21] Appl. No.: 412,680

[22] Filed: Mar. 29, 1995

[51] Int. Cl.$^6$ .................................................. A61B 17/32
[52] U.S. Cl. ............................ 606/171; 606/176; 30/392
[58] Field of Search .................................... 606/177, 178, 606/176, 171, 380, 179; 30/392–394, 82

[56] References Cited

U.S. PATENT DOCUMENTS

| | | |
|---|---|---|
| 493,730 | 3/1893 | MacKenzie . |
| 640,108 | 12/1899 | Dalzell ........................ 606/179 X |
| 1,123,730 | 1/1915 | Greenfield . |
| 1,626,553 | 4/1927 | Radtke . |
| 3,269,010 | 8/1966 | Bettcher . |
| 3,905,374 | 9/1975 | Winter . |
| 3,952,412 | 4/1976 | Rhodes . |
| 4,069,824 | 1/1978 | Weinstock . |
| 4,409,973 | 10/1983 | Neufeld . |
| 4,596,243 | 6/1986 | Bray . |
| 4,649,918 | 3/1987 | Pegg et al. . |
| 4,708,133 | 11/1987 | Comparetto . |
| 4,736,742 | 4/1988 | Alexson et al. . |
| 4,768,504 | 9/1988 | Ender . |
| 4,819,334 | 4/1989 | Mongeon . |
| 4,922,612 | 5/1990 | Greenwood . |
| 4,936,313 | 6/1990 | Burkhardt et al. . |
| 4,955,888 | 9/1990 | Slocum . |
| 5,077,902 | 1/1992 | Hitt . |
| 5,092,875 | 3/1992 | McLees . |
| 5,197,918 | 3/1993 | Klaassen ........................ 30/380 X |
| 5,197,967 | 3/1993 | Wilson . |
| 5,257,996 | 11/1993 | McGuire . |
| 5,320,115 | 6/1994 | Kenna . |
| 5,391,170 | 2/1995 | McGuire et al. . |
| 5,496,325 | 3/1996 | Mc Lees . |

FOREIGN PATENT DOCUMENTS

| | | |
|---|---|---|
| 0 432 325 | 6/1991 | European Pat. Off. . |
| 2460127 | 1/1981 | France . |
| 354343 | 6/1922 | Germany . |
| 8603213 | 12/1986 | Netherlands . |
| 591548 | 8/1947 | United Kingdom . |
| 754396 | 8/1956 | United Kingdom . |
| WO 89/09028 | 10/1989 | WIPO . |

OTHER PUBLICATIONS

Article entitled "Harvesting of Patella Tendon Graft for ACL Reconstruction using a Helical Tube Saw", by P.J. Dobson, FRACS, South Australia, 5 pages.

*Primary Examiner*—Jeffrey A. Schmidt
*Assistant Examiner*—Patrick W. Rasche
*Attorney, Agent, or Firm*—Gene Warzecha

[57] ABSTRACT

A ring blade and drive system, and method of using same, for harvesting bone-tendon-bone ligament grafts having substantially cylindrical bone plugs. The ring blade disclosed is a circular ring having a predetermined arcuate gap formed in its periphery. The drive system includes a blade holder to peripherally hold the ring blade and a fixed-center oscillating mechanism to oscillate the ring blade about its axis within a predetermined arcuate range of motion. The ring blade structure enables the production of a substantially cylindrical bone plug of unlimited length. Harvesting of a bone-tendon-bone ligament graft is facilitated with the ring blade and method disclosed which enables the ring blade to be placed partially around a tendon segment to create bone plugs aligned with the tendon fibers included in the defined tendon segment. The cuts into the bone may be initiated into the bone at either end of the tendon segment from the tendon side through to the exterior of the bone to which the tendon is attached.

3 Claims, 17 Drawing Sheets

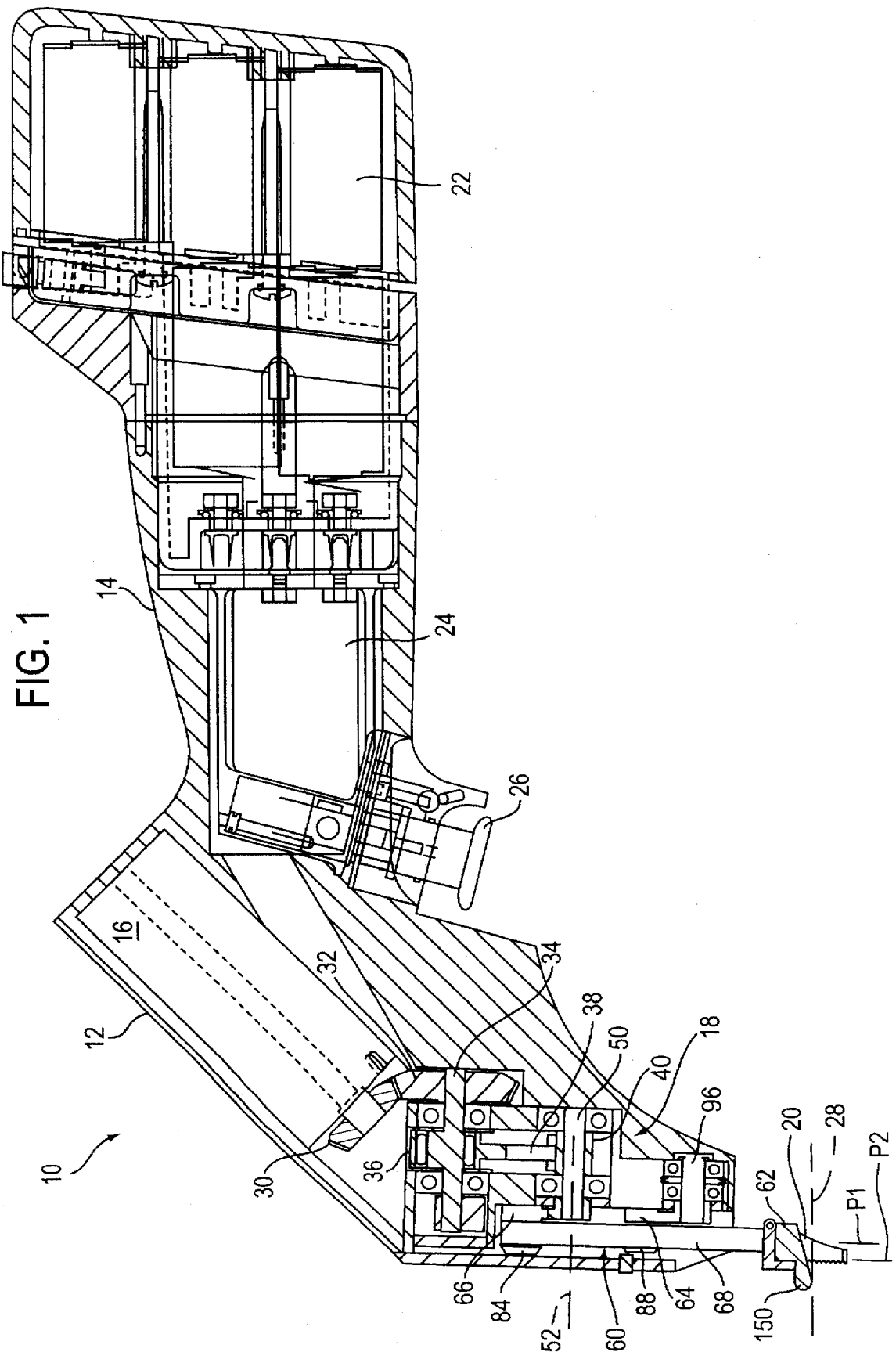

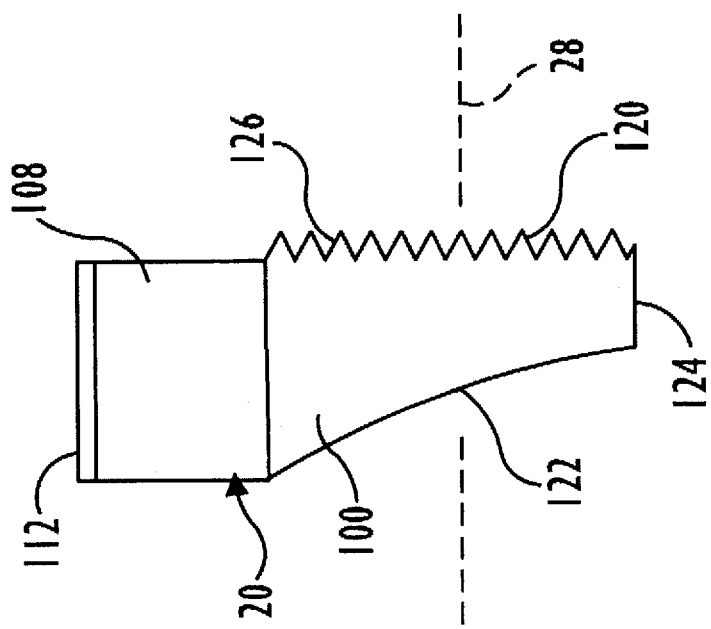
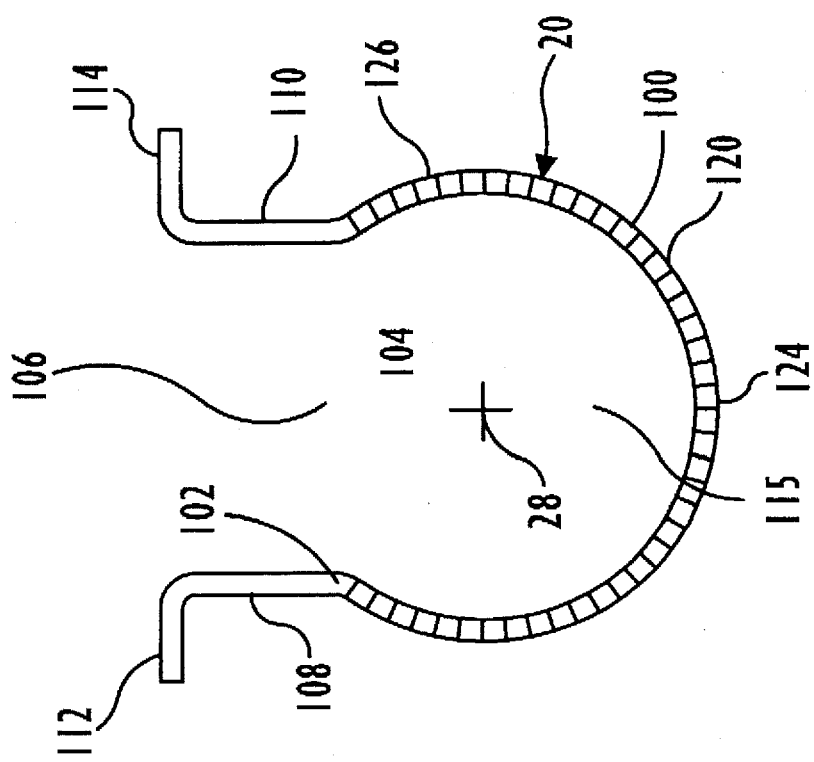

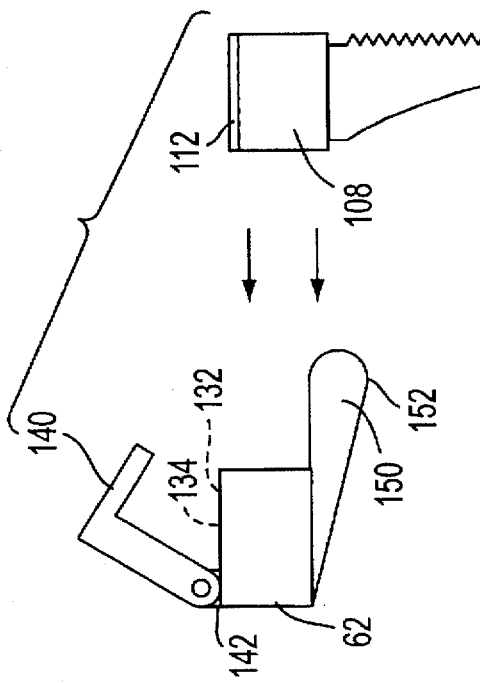
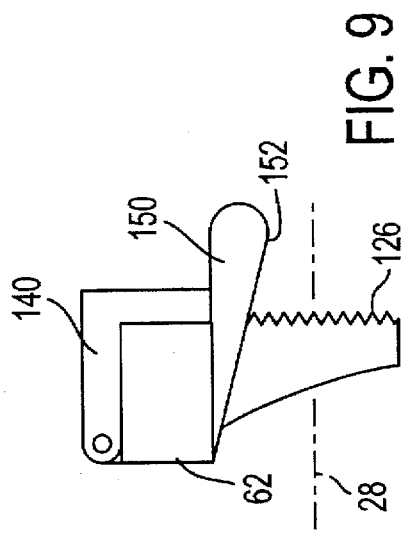
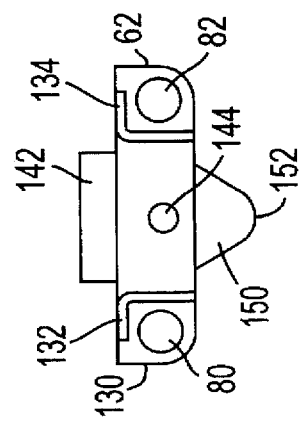

APPARATUS AND METHOD FOR HARVESTING A BONE-TENDON-BONE LIGAMENT GRAFT

BACKGROUND OF THE INVENTION

1. Field of the Invention

The invention relates generally to surgical saws. In particular, the invention relates to a system including a unique drive mechanism and a uniquely shaped surgical saw blade adapted to cut a generally cylindrical bone plug. More particularly, the invention relates to a surgical saw and method for harvesting a bone-tendon-bone ligament graft.

2. Description of the Prior Art

In certain surgical procedures bone blocks are cut from the bone at the end of a tendon to produce an artificial ligament in the form of a bone-tendon-bone graft. For example, for use in cruciate ligament reconstruction, bone-tendon-bone ligament grafts are often created by cutting a bone block from the patella and tibia and including a portion of the tendon extending between these two bones. Such a graft is then inserted into and secured within prepared bone tunnels in the tibia and femur in order to simulate the function of anterior or posterior cruciate ligaments. The bone plugs are generally secured within the bone tunnel by an interference screw which is threaded into the space between the bone plug and the tunnel wall. Since the bone tunnels are generally prepared by reamers, drills or core drills, the cross-section of the bone tunnels is circular. However, known methods of harvesting bone-tendon-bone ligament grafts produce bone plugs having generally rectilinear shapes which are then shaped to better fit in the tunnels. The production of a bone-tendon-bone graft generally involves cutting two parallel incisions on each side of the middle third of the patellar tendon and then making a three-sided, rectangular cut in the bone at each end of the tendon. An osteotome is then used to remove the bone blocks. Each bone block must then be trimmed to fit within the cylindrical bone tunnel which is typically on the order of 8–10 mm in diameter. While most known methods for producing bone-tendon-bone ligament grafts result in the preparation of bone plugs having a generally trapezoidal or other rectilinear cross-section, it is often preferred to have bone plugs having a cylindrical cross-section in order to produce a better fit between the bone plug and the pre-drilled bone tunnel into which the bone plug must fit. It is desirable to have the bone plugs conform to the shape of the bone tunnel as much as possible in order to promote healing and bony ingrowth of the plug into the tunnel wall.

The preparation of cylindrical bone plugs is known since various surgical procedures often require the preparation of cylindrical or substantially cylindrical bone plugs. Such bone plugs are generally created with the use of devices or instruments commonly referred to as trephines, circular bone saws, core drills, etc. In most of these applications, the circular cross-section of the cylindrical bone plug lies perpendicular to the axis of the circular device. Such devices are either unsuitable or difficult to use in the production of bone-tendon-bone ligament grafts.

One known device for harvesting the bone of a bone-tendon-bone graft is disclosed in U.S. Pat. No. 5,320,115 (Kenna). This device incorporates a powered saw having a cylindrical core drill which is oscillated about its axis and introduced into the bone at each end of the tendon in a direction toward the tendon. After the bone is cut, the core drill must be removed and used to cut the other bone, again toward the tendon. The core drill must be tilted as it is advanced in order to produce the relatively cylindrical bone plug and avoid cutting the tendon.

Another saw adapted to produce cylindrical bone plugs is disclosed in U.S. Pat. No. 5,092,875 (McLees). This patent discloses a circular blade having a peripheral drive arm extending radially outwardly from the body of the blade. The drive arm is oscillated along a semi-circular arc so that the circular blade oscillates about its axis and is able to cut a continuous length of cylindrical bone plug. While this device is capable of producing a bone-tendon-bone graft with cylindrical bone plugs, in actual practice this device is difficult to use. Moreover, the method shown in this patent does not facilitate the production of a partially cylindrical graft which may be desirable in certain situations.

Because bone plugs are often secured by interference screws inserted into the space between the plug and the tunnel wall, totally cylindrical bone plugs may not be desirable. Other applications may find totally cylindrical bone plugs desirable, but for many bone-tendon-bone ACL reconstructions the bone plugs should be produced with a flat so a space remains between the plug and the tunnel wall into which an interference screw will fit. No known prior art devices can easily produce such a plug shape in a bone-tendon-bone graft.

It is accordingly an object of this invention to produce a bone saw system for harvesting a bone-tendon-bone graft.

It is also an object of this invention to produce a flat, ring blade capable of cutting tissue by oscillating about its axis.

It is a further object of this invention to produce a ring blade capable of beginning the cut into a bone at either end of a tendon from the tendon side of the bone.

It is also an object of this invention to produce a bone saw system in which the blade may be attached to the drive unit after the blade has been properly positioned adjacent tissue to be cut.

It is an additional object of this invention to produce a ring blade capable of being easily attached and detached from a drive unit.

It is an object of this invention to produce a bone saw which can produce a substantially cylindrical bone plug of any desired length.

It is an object of this invention to produce a bone saw which can produce a substantially cylindrical bone plug having a flat surface along one side thereof, the size of this flat surface being controllable.

It is also an object of this invention to produce a ring blade capable of being attached to a drive unit in a selected direction so that the cut may be produced by either a pulling motion or a pushing motion.

It is also an object of this invention to produce a ring blade adapted to enable the formation of a longitudinally curved surface along a selected point of the bone plug.

It is an additional object of this invention to provide a method of harvesting a bone-tendon-bone plug through the use of a ring blade.

It is also an object of this invention to produce a bone saw system and method for harvesting a bone-tendon-bone graft such that the bone portions of the graft are aligned with the width of the tendon at each end of the graft.

SUMMARY OF THE INVENTION

These and other objects of this invention are achieved by the preferred embodiment disclosed herein which comprises a cutting blade, generally referred to herein as a ring blade, for harvesting a substantially cylindrical bone plug, the ring blade comprising a substantially circular ring having an axis, a periphery with a predetermined arcuate gap in the periphery and opposing axially aligned edges. The ring blade has a cutting means on at least one of the axially aligned edges which is adapted to make an arcuate cut.

The invention also comprises a surgical system for harvesting a bone-tendon-bone graft comprising a ring blade, as described above and a handpiece for driving the ring blade. The handpiece comprises a power source, a fixed-center oscillating means and a drive transfer means for transferring the output of the power source to the fixed-center oscillating means.

The invention also is an embodiment of the method of harvesting a bone-tendon-bone graft from a patellar tendon. The method comprises the steps of providing a ring blade, as described above, providing a drive means for peripherally oscillating the ring blade about its axis, making a pair of parallel incisions in the patellar tendon and passing the ring blade through the incisions to place it in an orientation with its cutting edge substantially under the tendon. The ring blade is then attached to the drive means and urged through the bone at a selected end of the patellar tendon.

BRIEF DESCRIPTION OF THE DRAWINGS

FIG. 1 is a side elevation diagrammatic view in cross-section of a surgical bone saw system constructed in accordance with the principles of this invention.

FIG. 4 is a front elevation view of the ring blade used in the system shown in FIG. 1.

FIG. 5 is a side elevation view of FIG. 4.

FIG. 6 is a front elevation view of a blade holder.

FIG. 7 is an exploded side elevation view showing how the ring blade of FIG. 4 is assembled with the blade holder of FIG. 6.

FIG. 8 is a front elevation view of the blade holder of FIG. 6 with a latching cover.

FIG. 9 is a side elevation view of the ring blade/blade holder assembly showing the latching cover in place.

DESCRIPTION OF THE PREFERRED EMBODIMENT

Figure 3:
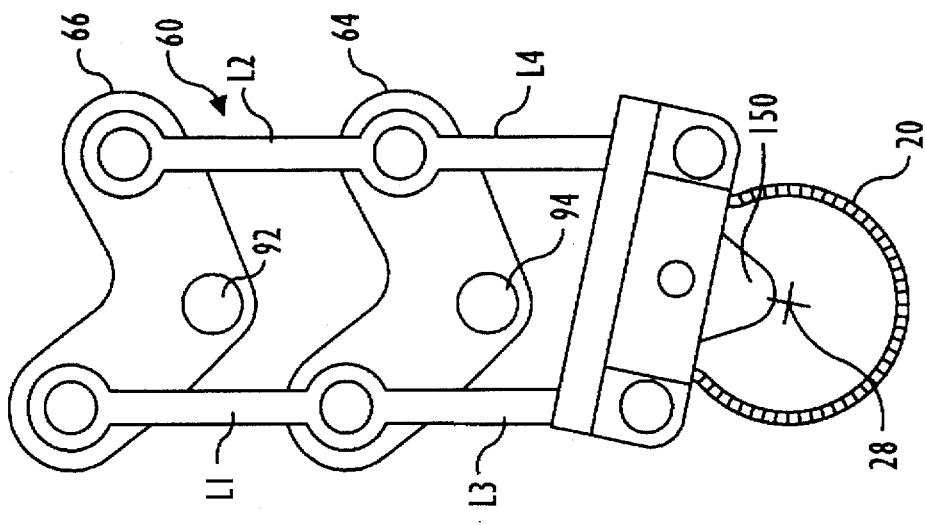
FIG. 3 shows the fixed-center oscillating mechanism of FIG. 2 at a particular point in its cycle of operation.

As shown in FIG. 1, surgical saw system 10 comprises a handpiece 12 having a handle 14, a motor 16 and a drive mechanism 18 for driving a ring blade 20. In the preferred embodiment, handpiece 12 is part of a battery operated system which further comprises a battery pack 22 and is controlled by a motor control circuit 24 and activated by a trigger 26 in a conventional manner. As will be understood, the function of system 10 is to produce a fixed-center oscillating motion of ring blade 20 so that a bone-tendon-bone graft may be easily produced with substantially cylindrical bone plugs at each end of a connecting tendon.

Drive mechanism 18 comprises those components necessary to convert the rotary motion of the drive shaft of motor 16 into a fixed-center oscillating motion of blade 20. The term "fixed-center" is used to refer to the fact that ring blade 20 can cut through a surface merely by oscillating around its axis 28 within a plane perpendicular to the axis, i.e. its center is fixed since no translational motion of the axis is required to produce this oscillation. Since those skilled in the art will understand the operation of drive mechanism 18 without a detailed explanation of each of the components (i.e. bearings, etc.), only the main components will be described. In the preferred embodiment, drive mechanism 18 comprises a bevel gear 30 secured to the drive shaft of motor 16 and another bevel gear 32 operatively connected to bevel gear 30 in order to transfer the rotary motion to a first horizontal drive shaft 34 on which is mounted an eccentric gear 36. Eccentric gear 36 is joined by a connecting rod 38 to a crank assembly 40 which is in turn connected to a second horizontal drive shaft 50. The function of components 30 to 40 is to convert the rotary motion of motor 16 to an oscillating motion of drive shaft 50 which, in the preferred embodiment, oscillates about its axis 52 within a range of ±12°. It will be understood by those skilled in the art that, while drive mechanism 18 is constructed as described in order to operate within handpiece 12 which has been ergonomically designed for the particular application of harvesting bone-tendon-bone grafts from a human knee, numerous other embodiments could be devised for producing the oscillatory motion of drive shaft 50.

Figure 2:
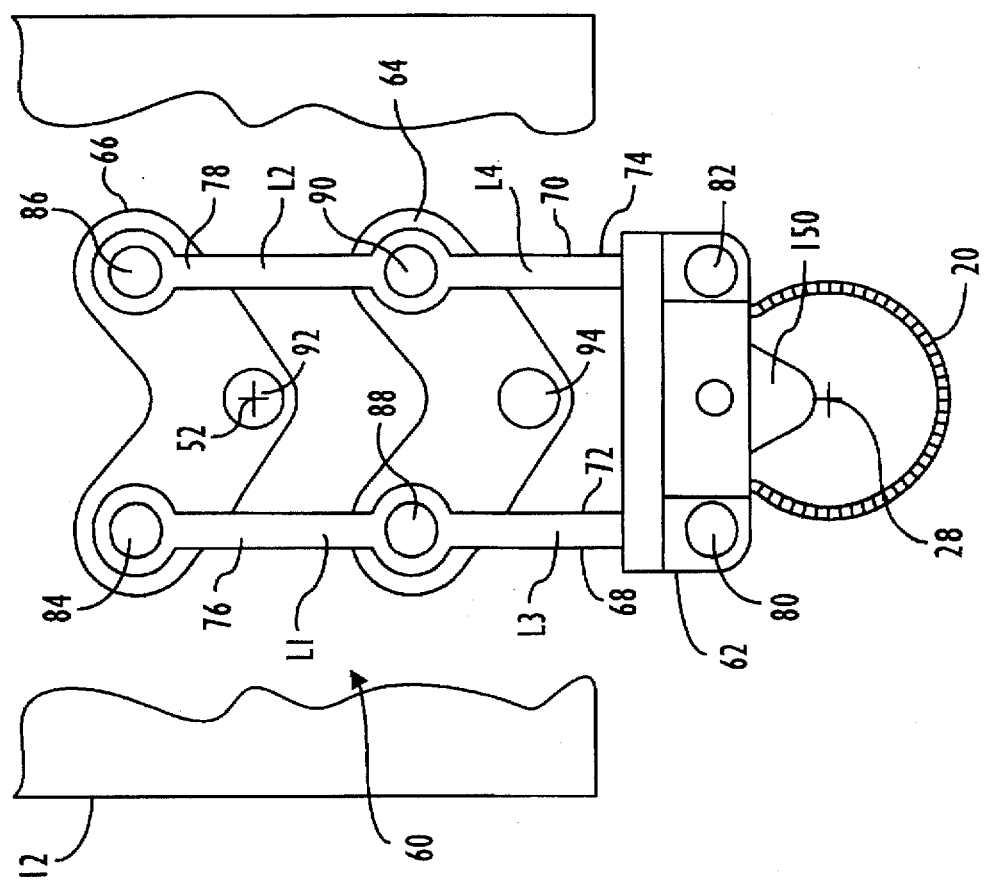
FIG. 2 is a cut-away front elevation view of a portion of FIG. 1 showing the fixed-center oscillating mechanism used in the preferred embodiment.

The oscillating output of drive mechanism 18 is the input to fixed-center oscillating subassembly 60 which converts the oscillatory motion of drive shaft 50 into the fixed-center oscillating motion of blade 20. Referring to FIGS. 2 through 4, it will be noted that subassembly 60 comprises a blade holder or frame 62, a first bracket 64 and a second bracket 66. The first and second brackets are aligned in a common first plane P1 with a portion of blade holder 62. As described below in FIGS. 6 through 9, ring blade 20 is held securely within blade holder 62 so as to be aligned within a plane P2 parallel to plane P1. Connecting rods 68 and 70 pivotably join blade holder 62 and first and second brackets 64, 66. Each connecting rod 68 and 70 has a distal end 72 and 74, respectively, and a proximal end 76 and 78, respectively. Blade holder 62 is pivotably joined to distal end 72 at pivoting junction 80 and to distal end 74 at pivoting junction 82. The proximal ends 76 and 78 of the connecting rods are similarly pivotably joined to second bracket 66 at pivoting junctions 84 and 86, respectively. First bracket 64 is similarly pivotably joined to the connecting rods at a point along their lengths between second bracket 66 and blade holder 62 at pivotable junctions 88 and 90. The second bracket 66 is pivotably mounted on pivot point 92 and first bracket 64 is pivotably mounted on an idling pivot point 94, and the pivot points are fixedly mounted relative to housing 12. Pivot point 92 is also aligned with axis 52 and fixedly connected to drive shaft 50 so that the oscillatory motion of drive shaft 50 is converted into the oscillatory motion of second bracket 66. Pivot point 94 is essentially the axis of a support shaft 96 (best seen in FIG. 1) which is parallel to drive shaft 50. It will be understood that the various pivots and pivotable junctions include all the necessary bearings, sleeves, pins, etc. which may be required to perform the described function.

The lengths of the connecting rod sections between the pivot points produce a symmetrical structure about a line joining ring blade axis 28 with pivot points 92 and 94. Thus, length L1 between pivotable junctions 84 and 88 is equal to length L2 between pivotable junctions 86 and 90. Also, length L3 between pivotable junctions 80 and 88 is equal to the length L4 between pivotable junctions 82 and 90. As shown in FIG. 3, as second bracket 66 oscillates about its pivot point 92, first bracket 64 and blade holder 62 must necessarily follow with a similar oscillatory motion. The lengths L1, L2 need not equal the lengths L3, L4 to produce this motion.

The proximal ends of the connecting rods may be joined to any mechanism which can produce the desired motion of the ring blade. If a structure such as that shown in FIGS. 2 and 3 is used, the spatial relationship between the central pivot and the two pivotable junctions on one bracket is the same as that on the other bracket. That is, these points lie in a common plane at the vertices of a triangle on each bracket. This spatial, triangular relationship is the same as that between the axis 28 of the ring blade and the pivotable junctions on the blade holder. If suitably strong materials are used and if the connecting rods are restricted to maintain their vertical alignment as they reciprocate in response to the oscillatory motion of bracket 66, it may be possible to achieve the same operation with only one bracket.

It has been found that in order to achieve certain advantages of ring blades the ring may be formed with a predetermined annular gap which, as will be understood below, facilitates the use of the blade in the creation of bone-tendon-bone grafts. This annular gap results in the shape of the ring being substantially C-shaped rather than totally enclosed. However, it will be understood that the term "ring blade" as used herein is intended to mean all blades having circular peripheries including totally enclosed circular rings and C-shaped rings, unless otherwise specified.

As shown in FIGS. 4 and 5, ring blade 20 has a substantially circular body 100 having a periphery which has two ends 102 and 104, these ends defining an arcuate gap 106 therebetween. Body 100 encloses a circular open area 115 around axis 28. Each end 102 and 104 is attached to outwardly extending support portions comprising members 108 and 110, respectively, and the distal ends of these support members are bent outwardly into flanges 112 and 114, respectively. In the preferred embodiment, the body, support members and flanges are formed from a single flat piece of suitable material (e.g. steel, plastic, etc.) and aligned with axis 28 as best seen in FIG. 4. In an alternate embodiment best seen below in FIGS. 26a and 26b, the ends 102 and 104 are attached to or integrally formed with mounting blocks which provide a means to secure the ring blade to a blade holder and also serve as bearings for pivoting junctions 80 and 82. The size of the arcuate gap 106 and the distance between support members 108 and 110 is variable and a matter of choice depending upon the ultimate application for which the ring blade 20 is designed. Indeed, as will be noted below, alternate embodiments of a ring blade may be totally enclosed. Body 100 has a pair of oppositely facing, axially aligned front and back edges 120 and 122, respectively. As best seen in FIG. 5, body 100 is tapered so that its distal tip 124 is narrower than the remainder of the body. For ease of description the term "length" may be used to refer to those distances parallel to axis 28 and the term "width" may be used to refer to distances perpendicular to axis 28. Thus, the length of ring blade 20 at point 124 is shorter than its length adjacent support members 108 and 110. The curvature of back edge 122 facilitates the tilting of the ring blade in order to produce a curve in the cylindrical bone plug, as will be understood below. Front edge 120 is provided with a cutting means such as a plurality of cutting teeth 126 along that portion of the edge which is circular. The ring blade is capable of being used with its front, cutting edge pointed either toward or away from a user. Other cutting surfaces could equally be utilized so long as they could be adapted to cut the tissue with the slight oscillatory motion of ring blade 20. It will be understood that portions of the ring blade could be provided with different cutting surfaces depending upon the tissue to be cut. For example, smooth tissue would be more likely to be cut by a knife edge rather than a plurality of teeth. Furthermore, different cutting edges could be provided on different portions of the blade depending upon the particular application for which the system is to be used. One possible embodiment could include a bone cutting edge on either side of distal tip 124 with a soft tissue cutting edge adjacent each end of the bone cutting portion. Another ring blade embodiment could utilize a cutting edge on both front and back edges 120 and 122. If desired, the cutting edge on front edge 120 could be different from the one on the back edge.

The manner in which ring blade 20 is held within handpiece 12 is best understood by reference to FIGS. 6 through 9. Blade holder 62 is best seen schematically in FIG. 6 with various associated components removed. The blade holder is intended to hold the blade peripherally, from a point spaced from axis 28 to enable a peripherally oscillating drive means to produce a fixed-center oscillating motion. The term peripherally oscillating means any type of drive means that acts from a point outside the circular periphery of the ring blade. Blade holder 62 comprises a generally rectilinear body 130 having a pair of uniquely shaped, spaced slots or recesses 132 and 134 adapted to receive corresponding support members and flanges 108, 112 and 110, 114, respectively. The slot in blade holder 62 may be adapted to hold other shapes of support members and even totally circular blades (shown below in FIGS. 21 through 25). Additionally, blade holder 62 may be adapted to hold a modified ring blade having each of its ends encased within a plastic or other material having a chosen shape to fit into corresponding recesses in the blade holder. It will be noted that the symmetry of the holding device enables ring blade 20 to be placed in one of two positions, 180° apart, so the cutting edge 126 could face in either of two different directions. The body 130 of blade holder 62 has a locking device in the form of a cover 140 hingedly joined to a raised boss 142. A spring-loaded latch pin or ball 144 extends from the front of blade holder 62 to be received within a hole or detent 146 within the cover 140 when the latter is closed to hold ring blade 20 within slots 132 and 134.

A depth penetration gauge 150 is attached to the front of blade holder 62 and has a distal tip 152 which extends toward axis 28 of ring blade 20 as best seen in FIG. 9. The size of depth gauge 150 may be chosen to control the penetration of the blade into bone to produce a desirable size of bone plug. The depth gauge also serves as an anti-dive mechanism to minimize any tendency of ring blade 20 to cut too deeply into the bone. Such deep cuts could, if permitted to occur, cause wedging of the blade and excessive friction. The depth gauge 150 thus facilitates proper operation of the invention. It operates best when situated on the side of blade holder 62 adjacent the cutting edge 126 and spaced from the cutting edge by some distance which, in the preferred embodiment, is on the order of 0.125 inches.

Figure 10:
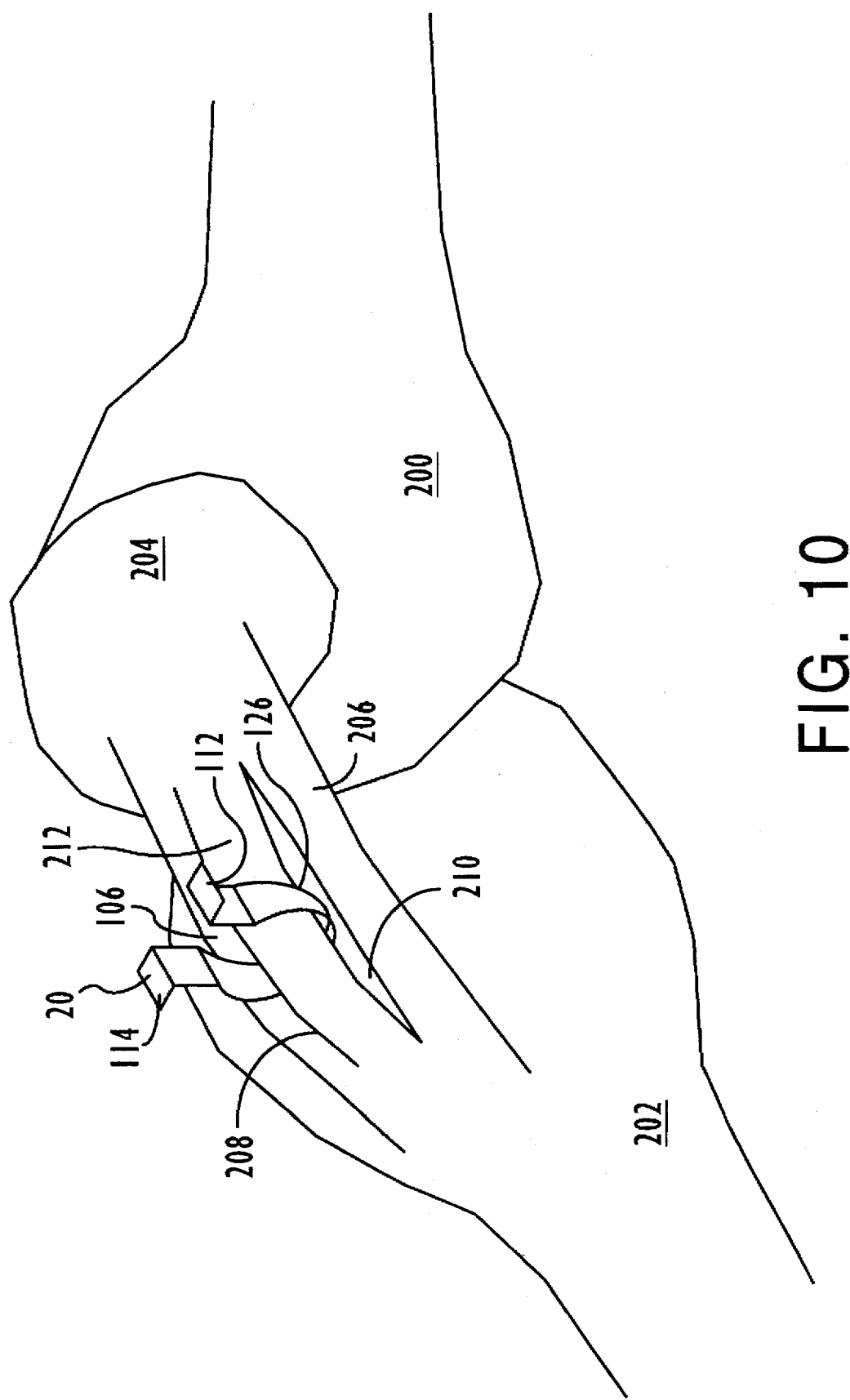
FIG. 10 is a diagrammatic view of one of the steps of the method of using the surgical saw system of FIG. 1.

A method of using the system 10 is shown in FIGS. 10 through 18. FIG. 10 shows one environment in which system 10 may be used as being a knee joint having a femur 200, a tibia 202, a patella 204 and a patellar tendon 206. In harvesting a bone-tendon-bone ligament graft from the patellar tendon 206, a portion of the patellar bone 204 is excised along with a portion of tibial bone 202 and the interconnecting portion 212 of patellar tendon 206. One method of forming the patellar tendon portion or segment 212 of the graft is to form a pair of parallel incisions 208 and 210 between the bone at the patella side of the tendon and the bone at the tibia side of the tendon. This portion is generally the central third of the patellar tendon ligament. Ring blade 20 may then be "wrapped" or placed partially around tendon portion 212 by passing the portion through annular gap 106 in order to place the cutting edge 126 substantially under tendon portion 212. Flanges 112 and 114 may then be secured within blade holder 62 in the manner shown in FIGS. 6 through 9 in order to continue the procedure. One advantage provided by the invention is that the longitudinally extending fibers of tibial portion 212 are assured to be aligned with the bone plug to which these fibers are attached because each bone plug is formed from the tendon side and out through the bone.

Figure 11:
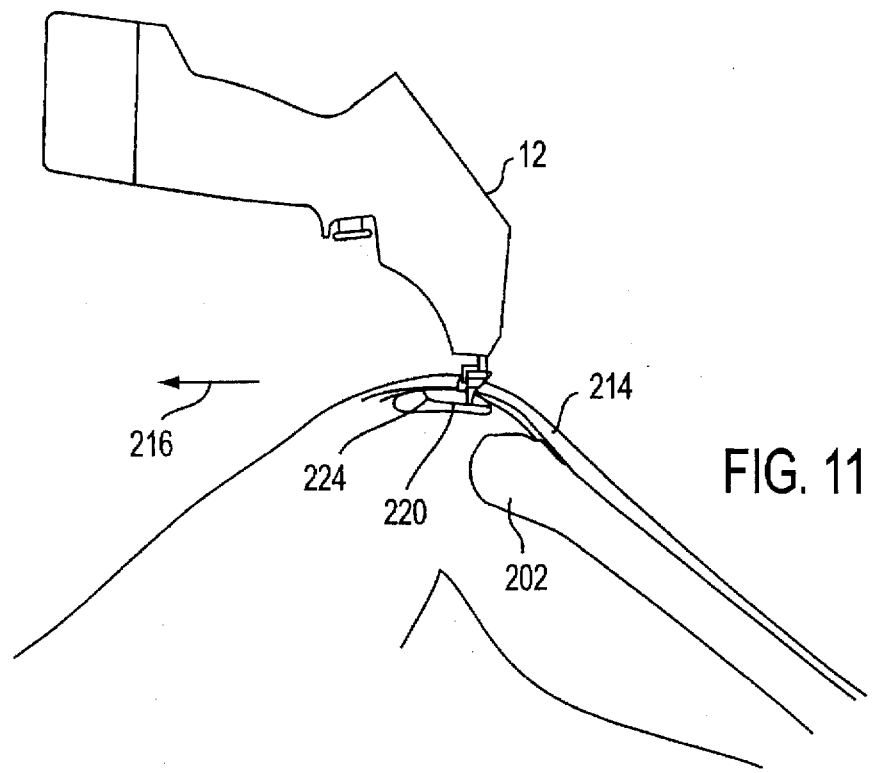
FIGS. 11, 12, 13 and 14 are diagrammatic views showing other steps in the method of using the invention on a human knee.
Figure 12:
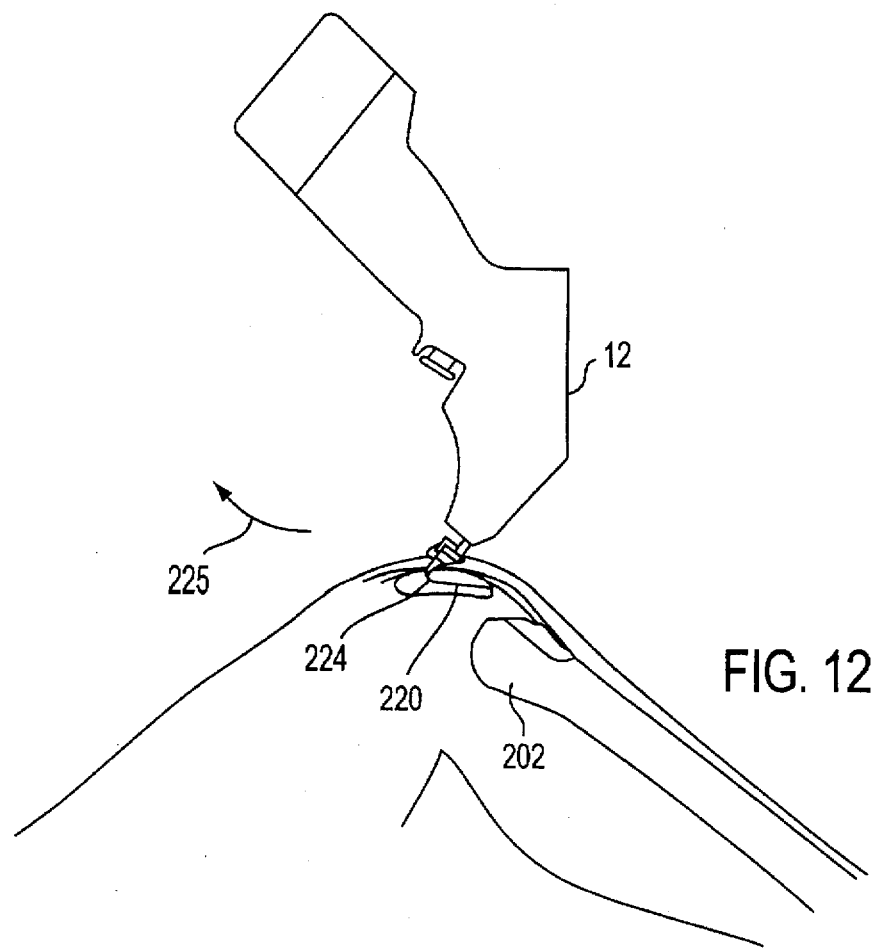
Figure 13:
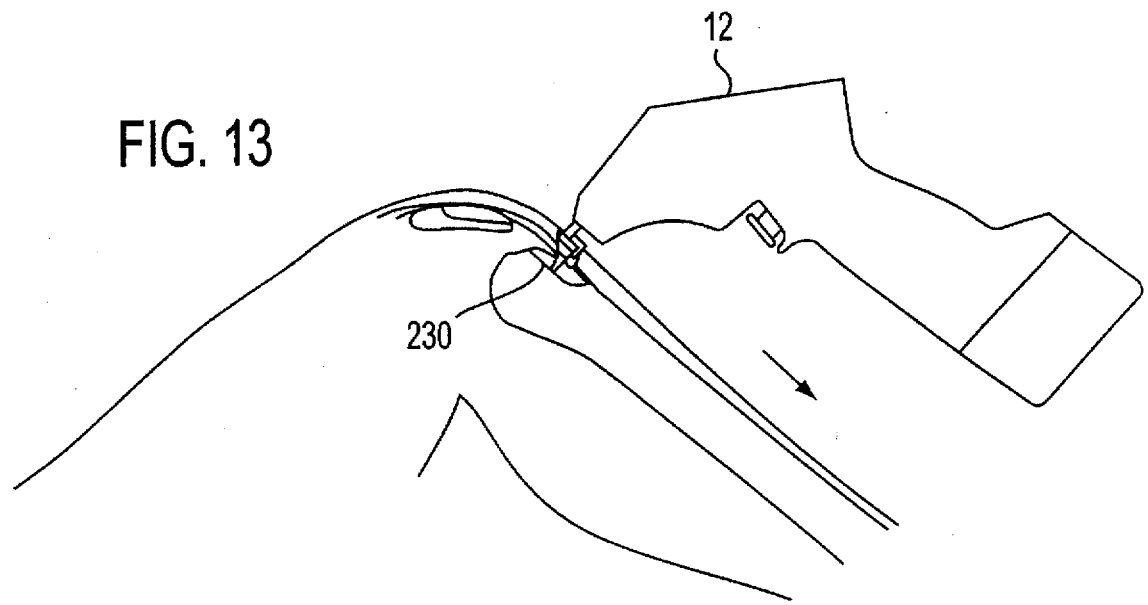
Figure 14:
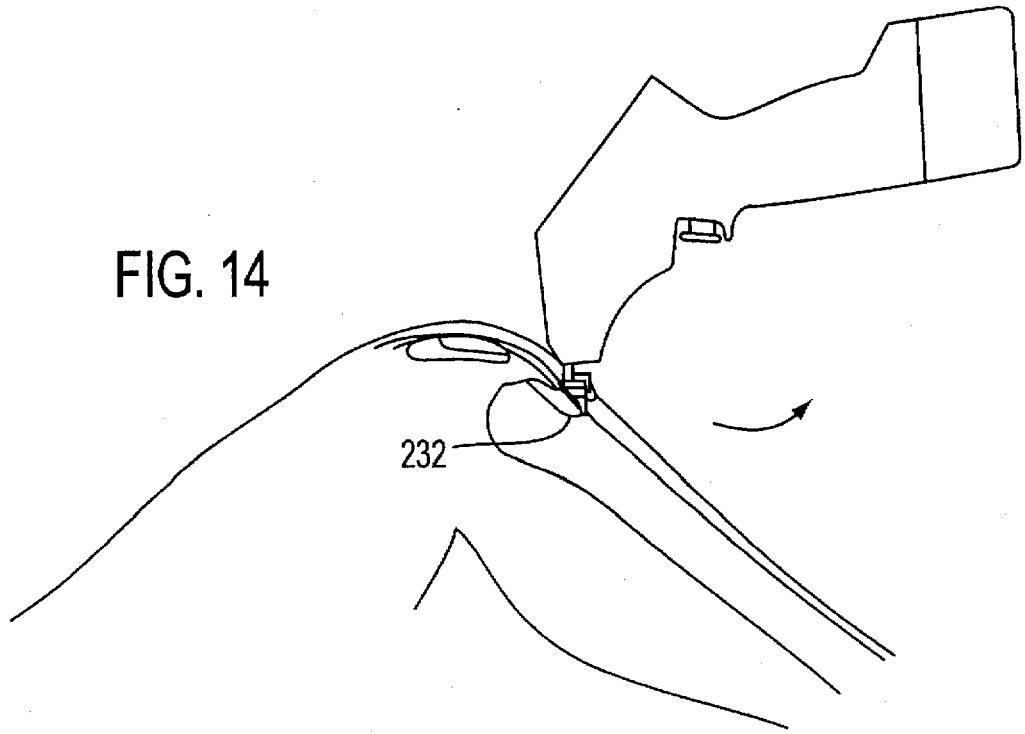
Figure 15:
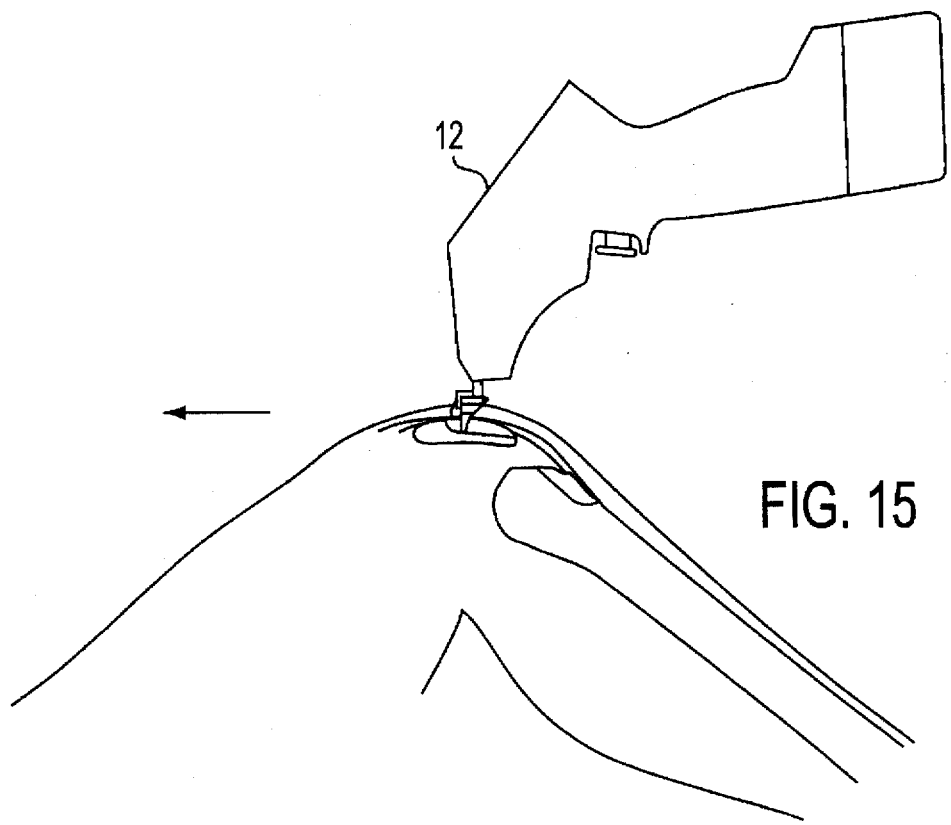
FIGS. 15, 16, 17 and 18 are diagrammatic views showing an alternative method of using the invention on a human knee.
Figure 16:
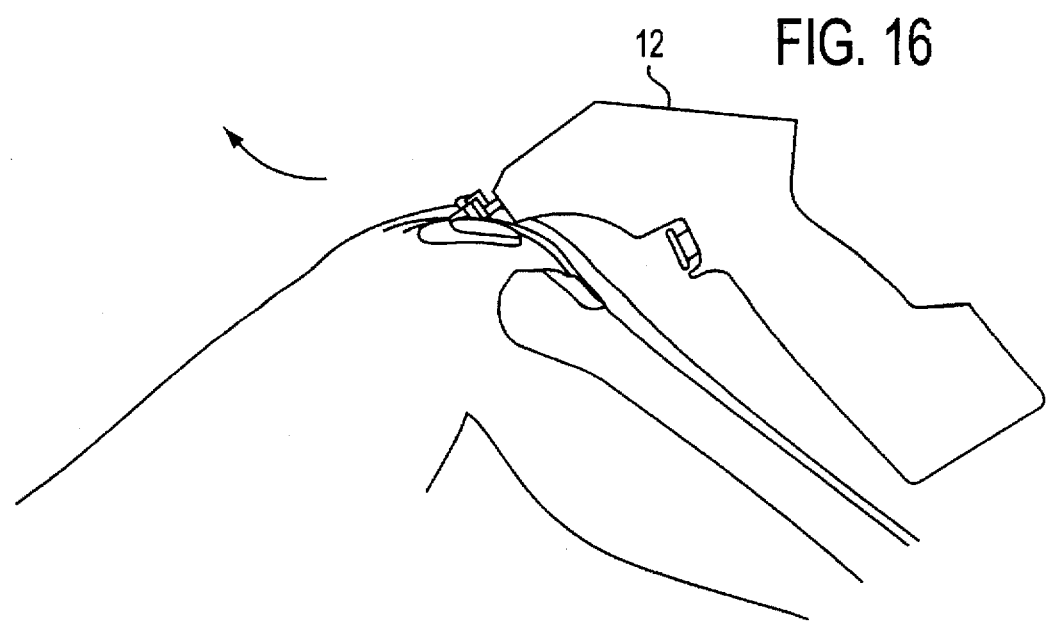
Figure 17:
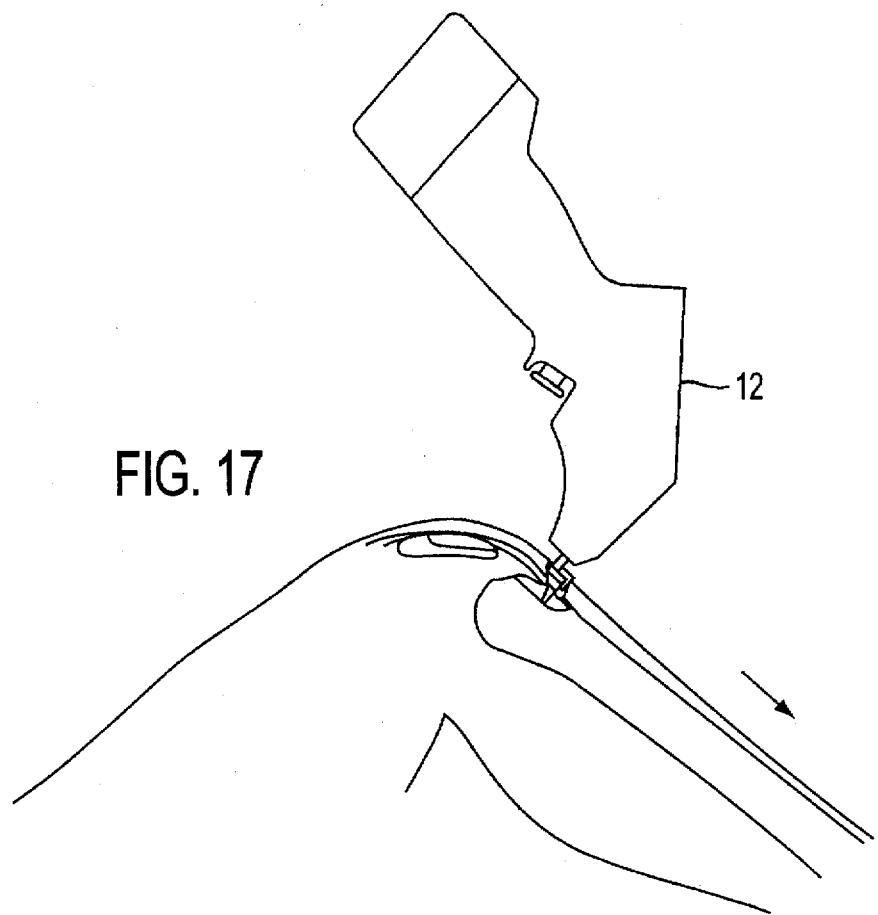
Figure 18:
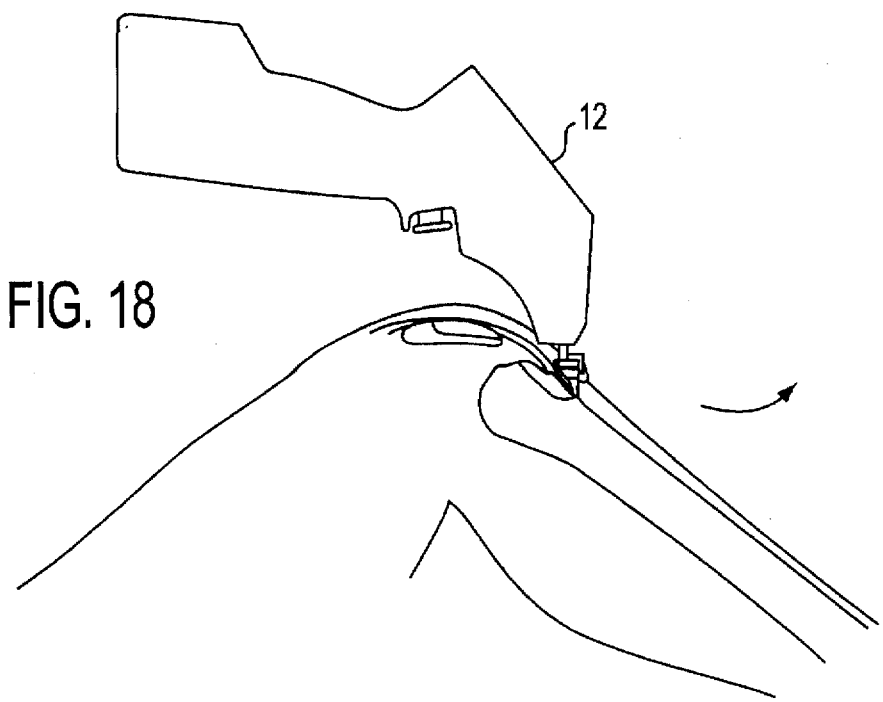

As shown in FIGS. 11 through 14, handpiece 12 with attached ring blade 20 may be used in a pulling fashion to cut both the tibial and patellar bone plugs from a human knee 214. In this procedure, the cutting edge of ring blade 20 is arranged to face toward the body of handpiece 12, and therefore toward the user so that a cutting action occurs on pulling the handpiece 12 toward the user in the direction of arrow 216. As shown in FIG. 11, the initial cutting action into the patellar bone produces straight annular cut 220 (best seen in FIG. 19) which is then smoothly joined to a curved annular cut 224 as handpiece 12 is tipped in the direction of arrow 225 as shown in FIG. 12 to cause blade 20 to exit the bone. Similarly, after the blade is disconnected from the handpiece and repositioned as shown in FIG. 13, the first cut into the tibia produces a straight cut 230 which is then curved at 232 as the handpiece is tilted to cause blade 20 to exit the bone.

If desired, ring blade 20 may be reversed to have the cutting edge facing away from the body of the handpiece as shown in FIGS. 15 through 18 so that both patellar and tibial bone plug sections could produced by a pushing action. In all other respects, the procedure shown in FIGS. 15 through 18 is similar to that shown in FIGS. 13 through 16. The surgical instrument shown in FIG. 1 is the one that is depicted in FIGS. 15 through 18 in the sense that it shows ring blade 20 facing away from a user holding handpiece 12. While the specific manner in which the blade may be repositioned 180° to face toward the user is not shown, those skilled in the art will understand how this may be accomplished.

Figure 19:
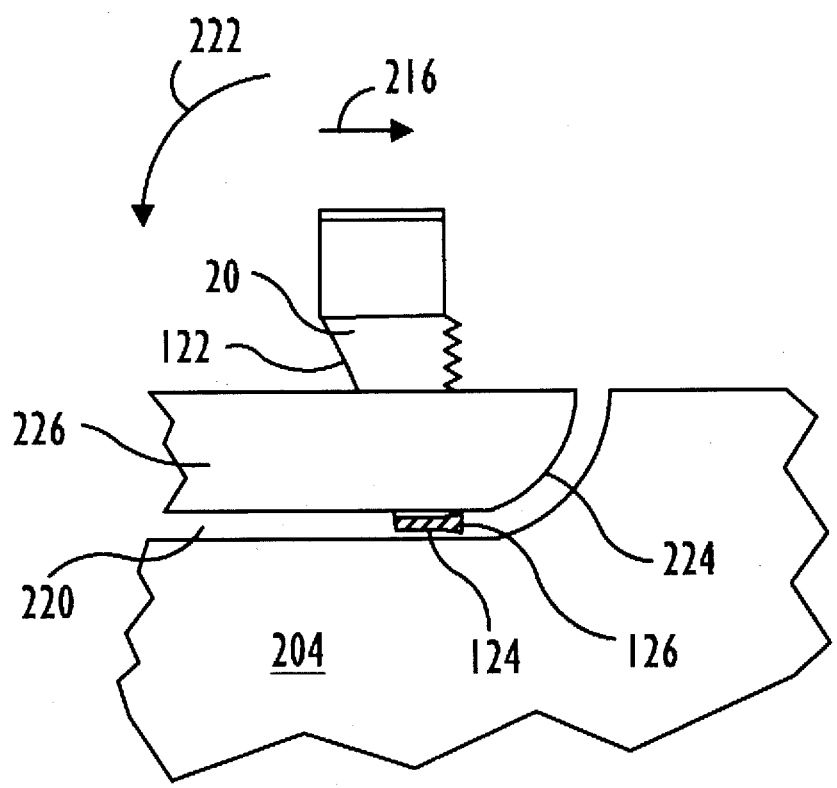
FIG. 19 is a diagrammatic view showing another step in the method of using the invention.

As diagrammatically shown in FIG. 19, ring blade 20 may be passed through patellar bone 204 in direction 216 (as also shown in FIG. 11) to create an annular cut 220 formed by the oscillating cutting edge of ring blade 20. The curved back edge 122 enables the handpiece (not shown) and blade 20 to be tilted, as shown by arrow 222, in order to guide the distal tip 124 of the ring blade in an arcuate manner to curve annular cut 220 upwardly to create a rounded end 224 in the patellar bone plug 226. For simplicity, the blade is shown only in one position but it will be understood that the annular cut 220 is formed as the blade moves through the bone. A similar procedure may be used to round the tibial bone plug (not shown).

Figure 20A:
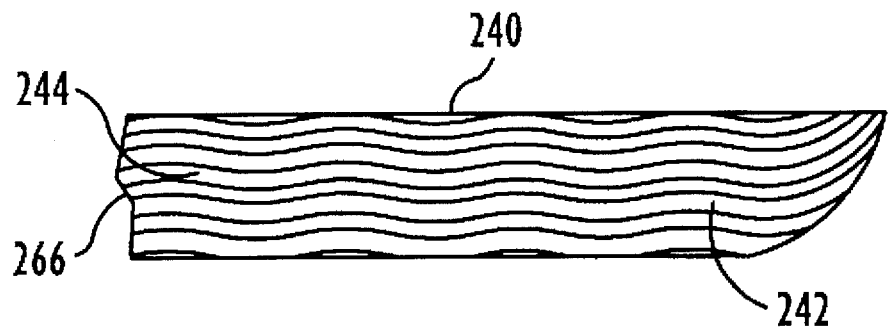
FIGS. 20a and 20b are diagrammatic views of the surface of a bone plug produced by the surgical saw system of FIG. 1.
Figure 20B:
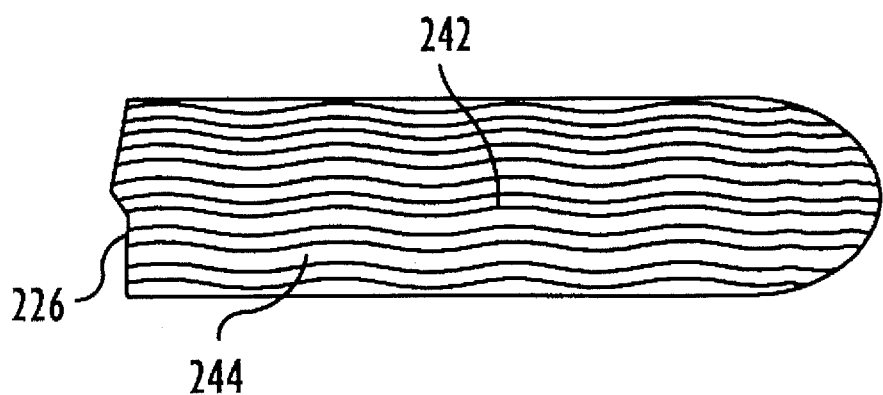
Figure 21A:
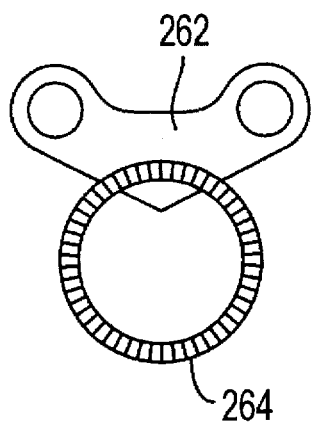
FIGS. 21a and 21b show a front elevation and side elevation view, respectively, of an alternate embodiment of a blade suitable for use with the invention.
Figure 21B:
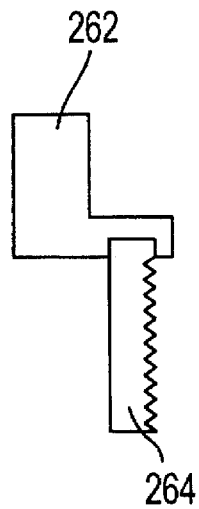

The resulting bone plug 226 is also shown in FIGS. 20a and 20b without the associated patellar tendon. The bone plug has a flat top surface 240 created because of depth gauge 150 and a cylindrical body surface 242 because of blade body 100. The texture of the cylindrical body surface may be varied by producing the cutting means at the front edge of ring blade 20 to create a desired cutting effect. For example, if teeth 126 are provided as shown in FIG. 4, the teeth may be set inwardly and outwardly relative to axis 28 (as best seen in FIG. 19) so that, upon oscillation of ring blade 20, a serrated pattern of grooves 244 will be formed in the surface of bone plug 226. Such serrations may enhance frictional engagement between the bone plug and its bone tunnel and may also assist in healing bony ingrowth. The teeth could be set in only one direction if desired (e.g. radially inwardly).

Figure 22A:
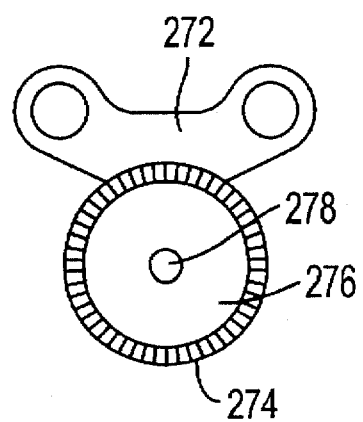
FIGS. 22a and 22b show a front elevation and side elevation view, respectively, of an alternate embodiment of a blade suitable fur use with the invention.
Figure 22B:
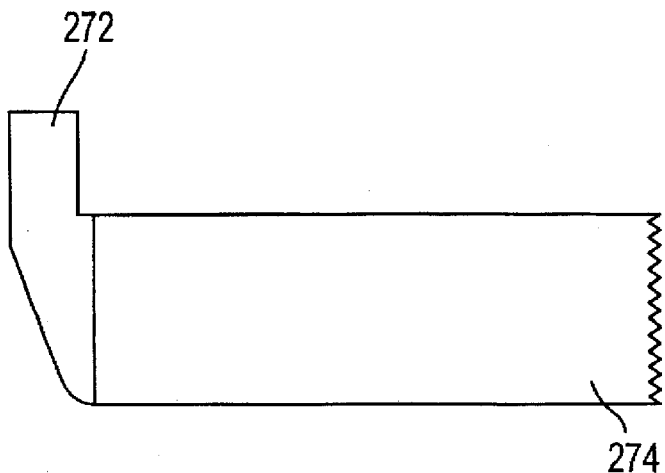
Figure 23A:
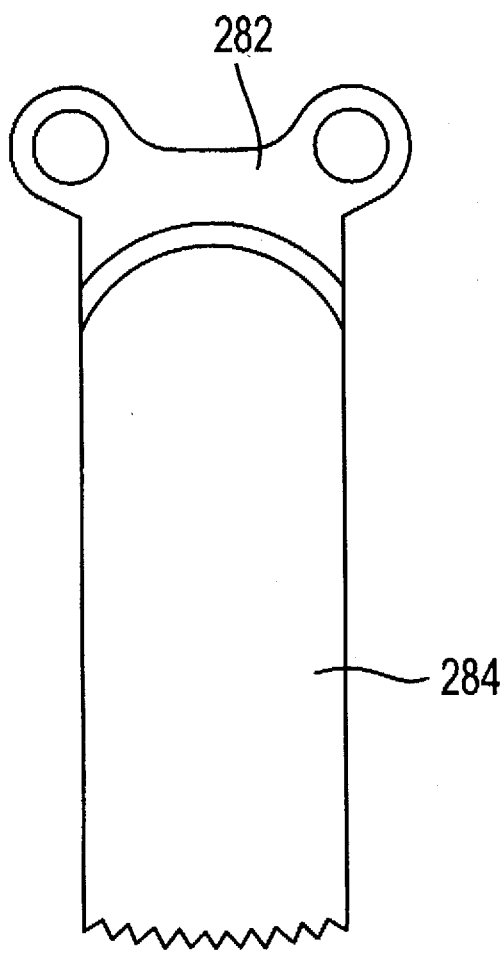
FIGS. 23a and 23b show front elevation and side elevation views, respectively, of an alternate embodiment of a blade suitable for use with the invention.
Figure 23B:
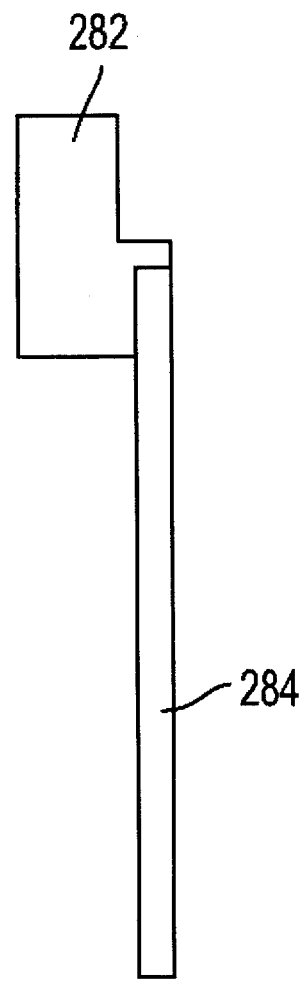

In addition to the preferred embodiment of the ring blade described above, the invention is easily adaptable to other blade configurations. For example, a modified ring blade holder 262 may be provided to serve as a peripheral attachment device to retain a totally circular ring blade 264 as shown in FIGS. 21a and 21b and 24a and 24b. The blade could be a fixed portion of the holder or it could be detachable therefrom. A similar blade holder 272 could be provided to hold an axially extended circular blade 274 as shown in FIGS. 22a and 22b. While this is similar to a prior art core drill, this embodiment enables the formation of a continuous length of cylindrical bone plug. Blade 274 could have a close back end surface 276 with an axial bore 278 to facilitate pushing a core out of the blade. Another possible configuration is blade holder 282 adapted to hold a flat oscillating blade 284 as shown in FIGS. 23a and 23b. Thus, it will be understood by those skilled in the art that a variety of blade styles could be produced to be used by a handpiece constructed in accordance with the principles of this invention.

Figure 24B:
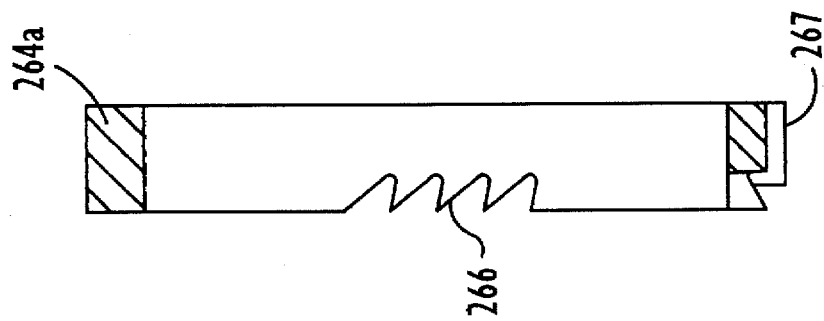
FIGS. 24a and 24b show front elevation and sectional elevation (along the line 24b—24b) views, respectively, of an alternate embodiment of a blade suitable for use with the invention.
Figure 24A:
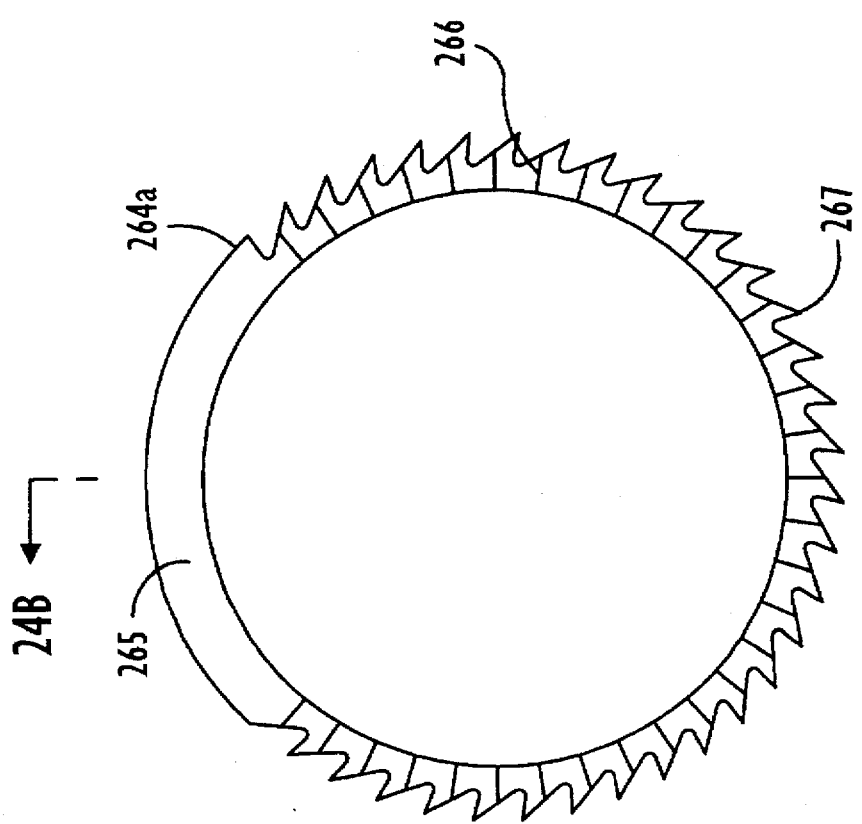

Variations in the teeth formed on the blades adapted for use with the system are also feasible, both on totally circular ring blades and on C-shaped ring blades. For example, as shown in FIGS. 24a and 24b, a circular blade 264a could have a smooth arcuate shank portion 265 adapted for enabling blade 264a to be clamped to an appropriately modified blade holder and the remaining portion of the annular body of blade 264a could be provided with axially facing teeth 266 and radially facing teeth 267. Such an arrangement would enable the blade to cut directly into the bone at one end of the patellar or tibial bone plug, in a plane perpendicular to the bone surface, and then be moved longitudinally along the bone plug to and through the tendon toward and through the other bone plug.

Figure 25B:
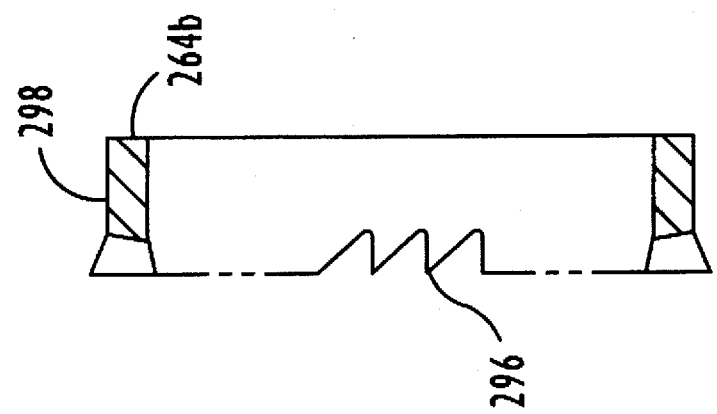
FIGS. 25a and 25b show a front elevation and sectional elevation (along the line 25b—25b) views, respectively, of an alternate embodiment of a blade constructed in accordance with the principles of this invention.
Figure 25A:
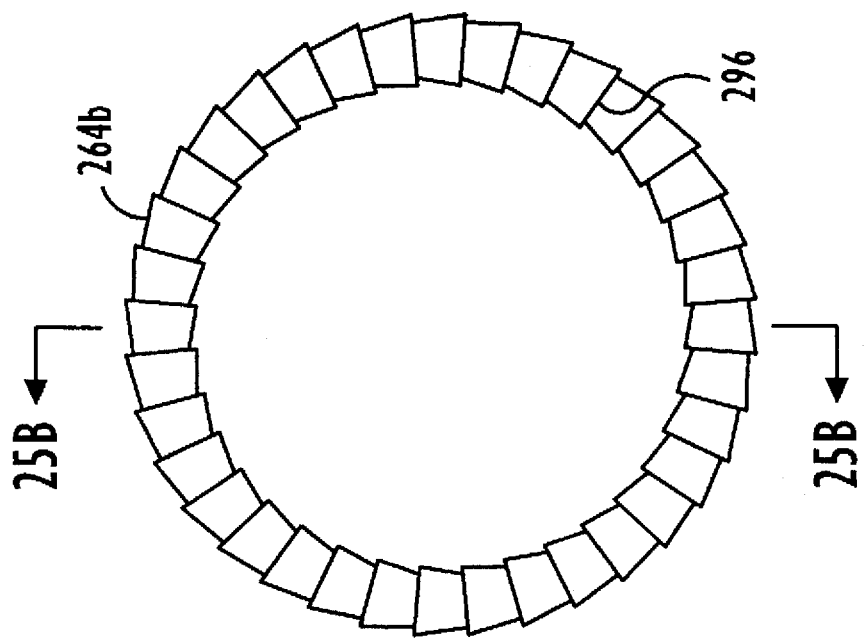

An alternative embodiment of ring blade 264b is shown in FIGS. 25a and 25b having a plurality of axially facing teeth 296 arrayed around the entire periphery of one edge of the blade. Such an arrangement would enable the body 298 behind the teeth to be smooth enough to be easily engageable by an appropriate clamping mechanism to hold it to a suitable blade holder.

The method of harvesting a bone-tendon-bone graft with a totally circular blade may be similar to any one of the methods described above except that the blade would need to first begin forming the graft from one end in the bone. The ring or circular blade could then be advanced through the bone to produce one bone plug, along the already cut tendon and through the bone at the other end to produce the other bone plug. Alternatively, the blade could be advanced through the bone on one side of the tendon and then retracted when the cut is completed. The blade could then be advanced through the bone at the other end and retracted once that cut is completed.

Figure 26A:
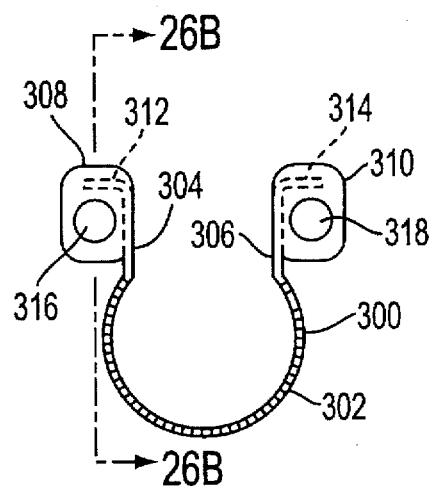
FIGS. 26a and 26b show front elevation and side elevation (along the line 26b—26b) views, respectively, of an alternate embodiment of a blade constructed in accordance with the principles of this invention.
Figure 26B:
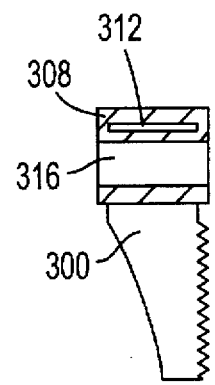
Figure 27:
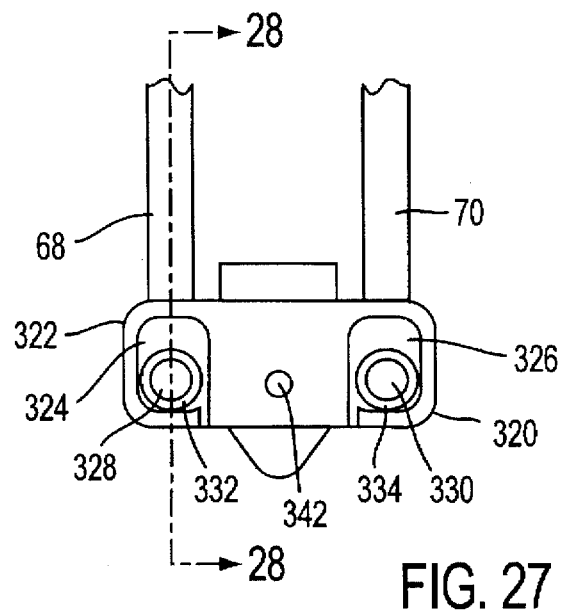
FIG. 27 is a front elevation view of a blade holder for use with the blade of FIGS. 26a and 26b.
Figure 28:
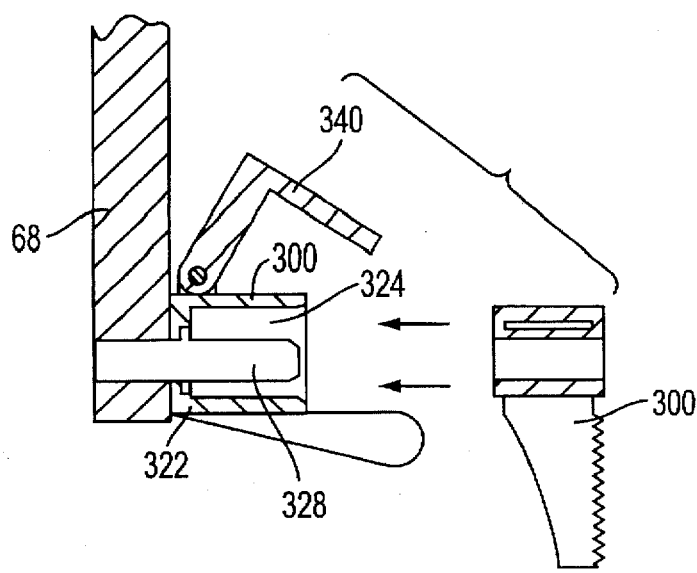
FIG. 28 is a side elevation view in cross-section of the blade holder of FIG. 27 (with a cover in open position) and the blade of FIGS. 26a and 26b.
Figure 29:
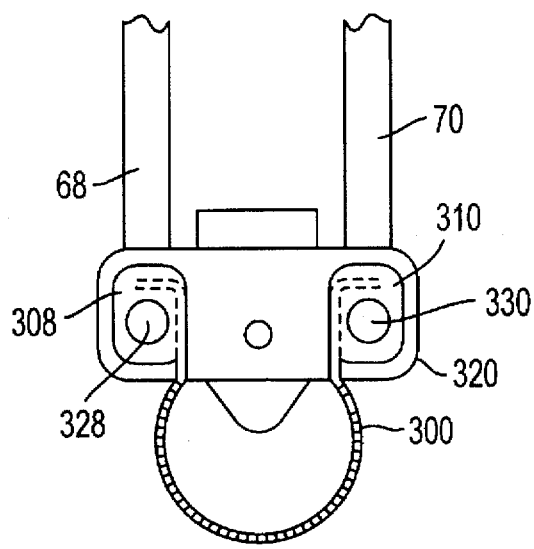
FIG. 29 is a front elevation view of the blade holder of FIG. 27 assembled with the blade of FIGS. 26a and 26b.
Figure 30:
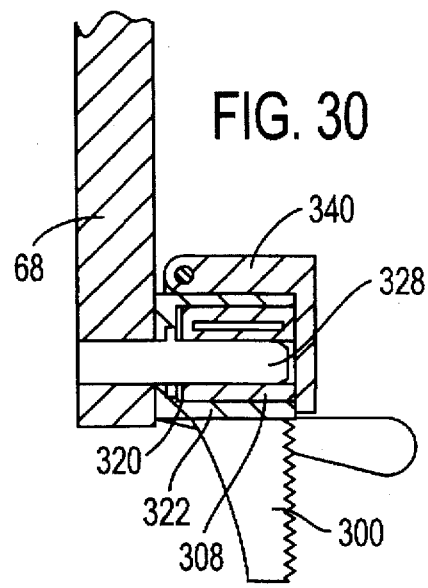
FIG. 30 is a side elevation view in cross-section of FIG. 29 showing a cover in place.
Figure 31:
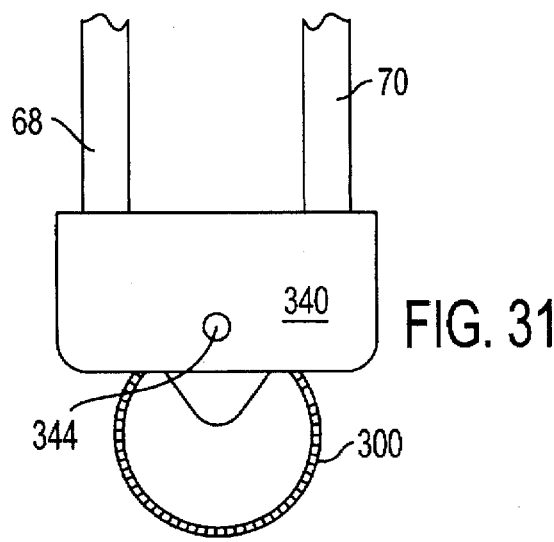
FIG. 31 is a front elevation view of FIG. 30.

Another alternative embodiment of the invention is shown in FIGS. 26a and 26b as ring blade 300 having a circular body 302 with ends 304 and 306 encased in injection molded block members 308 and 310, respectively. Block members 308 and 310 are molded around ends 312 and 314, respectively, and include cylindrical bores 316 and 318, respectively. Bores 316 and 318 provide simple bearings for coupling ring blade 300 to a complementarily shaped blade holder 320. As best seen in FIGS. 27 and 28, blade holder 320 is attached to the distal ends of connecting rods 68 and 70 (similarly to blade holder 62 shown in FIG. 2) and comprises a body 322, receiving recesses 324 and 326, and transversely fixed, polished pivot pins 328 and 330 secured to the connecting rods 68 and 70, respectively. The body 322 is retained adjacent the connecting rods by pin shoulders 332 and 334. When blade holder 320 and ring blade 300 are assembled, the proximal ends of pivot pins 328 and 330 fit into recesses 324 and 326, respectively, as best seen in FIGS. 29 and 30. Block members 308 and 310 may be formed from any suitable material capable of rigidly holding the body 302 and capable of forming recesses to serve as bearing surfaces about pivot pins 328 and 330. These bearing surfaces are replaced with each new ring blade as the old one is disposed of. Blade holder 320 is provided with a hinged locking cover 340 which is omitted for clarity in FIGS. 27 and 29, and is shown open in FIG. 28 and closed in FIGS. 30 and 31. Spring loaded ball or pin 342 on body 320 seats within recess 344 in cover 340 to hold the cover in place.

It will be understood that the bearing structure used in ring blade 300 is easily adaptable to the blades and corresponding blade holders shown in FIGS. 21 through 25.

It will be understood by those skilled in the art that numerous improvements and modifications may be made to the preferred embodiment of the invention disclosed herein without departing from the spirit and scope thereof.

What is claimed is:

1. A surgical system for harvesting a bone-tendon-bone graft comprising:
   a ring blade comprising a substantially cylindrical ring having an axis, a predetermined arcuate gap in the periphery thereof and opposing axially aligned edges;
   a cutting means on at least one of said axially aligned edges of said ring;
   a handpiece for peripherally supporting and driving said ring blade, said handpiece comprising a power source, a fixed-center oscillating means and a drive transfer means for transferring the output of said power source to said fixed-center oscillating means; and
   a radially elongated depth penetration gauge having a proximal end and a distal end, said proximal end fixed relative to said handpiece and said distal end spaced a predetermined axial distance from said cutting means and extending toward the axis of said ring blade.

2. A surgical system according to claim 1 further comprising:
   a blade holder for peripherally joining said ring blade to said fixed-center oscillating means comprising:
   a peripheral holding means provided with at least one recess to receive a portion of said ring blade; and
   a releasable locking means joined to said holding means to selectively close said recess to retain said portion of said ring blade therein.

3. A surgical system according to claim 2 wherein said ring blade has a pair of support members secured to said blade at each end of said predetermined arcuate gap, further comprising:
   a holding means provided with a pair of recesses, each complementarily shaped to receive a respective one of said support members.

* * * * *